United States Patent
Kutner et al.

(10) Patent No.: US 7,700,580 B2
(45) Date of Patent: Apr. 20, 2010

(54) PROCESS FOR PREPARATION OF PHARMACEUTICALLY PURE ANHYDROUS CALCIPOTRIOL

(75) Inventors: Andrzej Kutner, Warsaw (PL); Michal Chodyński, Pruszków (PL); Teresa Ryznar, Warsaw (PL); Hanna Fitak, Warsaw (PL); Jerzy Winiarski, Warsaw (PL); Bartlomiej Górecki, Warsaw (PL); Agnieszka Burzyńska, Zawiercie (PL); Wieslaw Szelejewski, Warsaw (PL)

(73) Assignee: Instytut Farmaceutyczny, Warsaw (PL)

( * ) Notice: Subject to any disclaimer, the term of this patent is extended or adjusted under 35 U.S.C. 154(b) by 0 days.

(21) Appl. No.: 11/813,211

(22) PCT Filed: Dec. 29, 2005

(86) PCT No.: PCT/PL2005/000087

§ 371 (c)(1), (2), (4) Date: Nov. 19, 2007

(87) PCT Pub. No.: WO2006/071129

PCT Pub. Date: Jul. 6, 2006

(65) Prior Publication Data

US 2008/0214876 A1    Sep. 4, 2008

(30) Foreign Application Priority Data

Dec. 30, 2004  (PL) .................................... 372013

(51) Int. Cl.
*A01N 37/36* (2006.01)

(52) U.S. Cl. ...................................... 514/167; 568/720
(58) Field of Classification Search .................. 514/167
See application file for complete search history.

(56) References Cited

U.S. PATENT DOCUMENTS

| 5,292,977 A | 3/1994 | Trost et al. |
| 2001/0056071 A1* | 12/2001 | Pelliccia et al. ............... 514/23 |
| 2004/0138184 A1* | 7/2004 | Schwartz et al. ............ 514/167 |

FOREIGN PATENT DOCUMENTS

| WO | 03/106412 A1 | 12/2003 |
| WO | 2004/046097 A1 | 6/2004 |

* cited by examiner

*Primary Examiner*—Porfirio Nazario Gonzalez
*Assistant Examiner*—Chukwuma O Nwaonicha
(74) *Attorney, Agent, or Firm*—Matthias Scholl, PC; Matthias Scholl

(57) ABSTRACT

A process for the preparation of a pharmaceutical-grade anhydrous calcipotriol comprising: (a) dissolving crude calcipotriol having a water content of X% by weight in a first solvent or in a mixture of two or more first solvents, said first solvent or said mixture of two or more first solvents forming an azeotropic system with water, to obtain a solution of crude calcipotriol; (b) obtaining an intermediate calcipotriol by (i) placing said solution of crude calcipotriol under a reduced pressure and evaporating, if X is greater than or equal to 1, or (ii) crystallizing, if X is lower than 1; and (c) re-dissolving said intermediate calcipotriol in a second solvent or a mixture of two or more second solvents, said second solvent being anhydrous, and crystallizing at least once to obtain pharmaceutical-grade anhydrous calcipotriol.

34 Claims, 1 Drawing Sheet

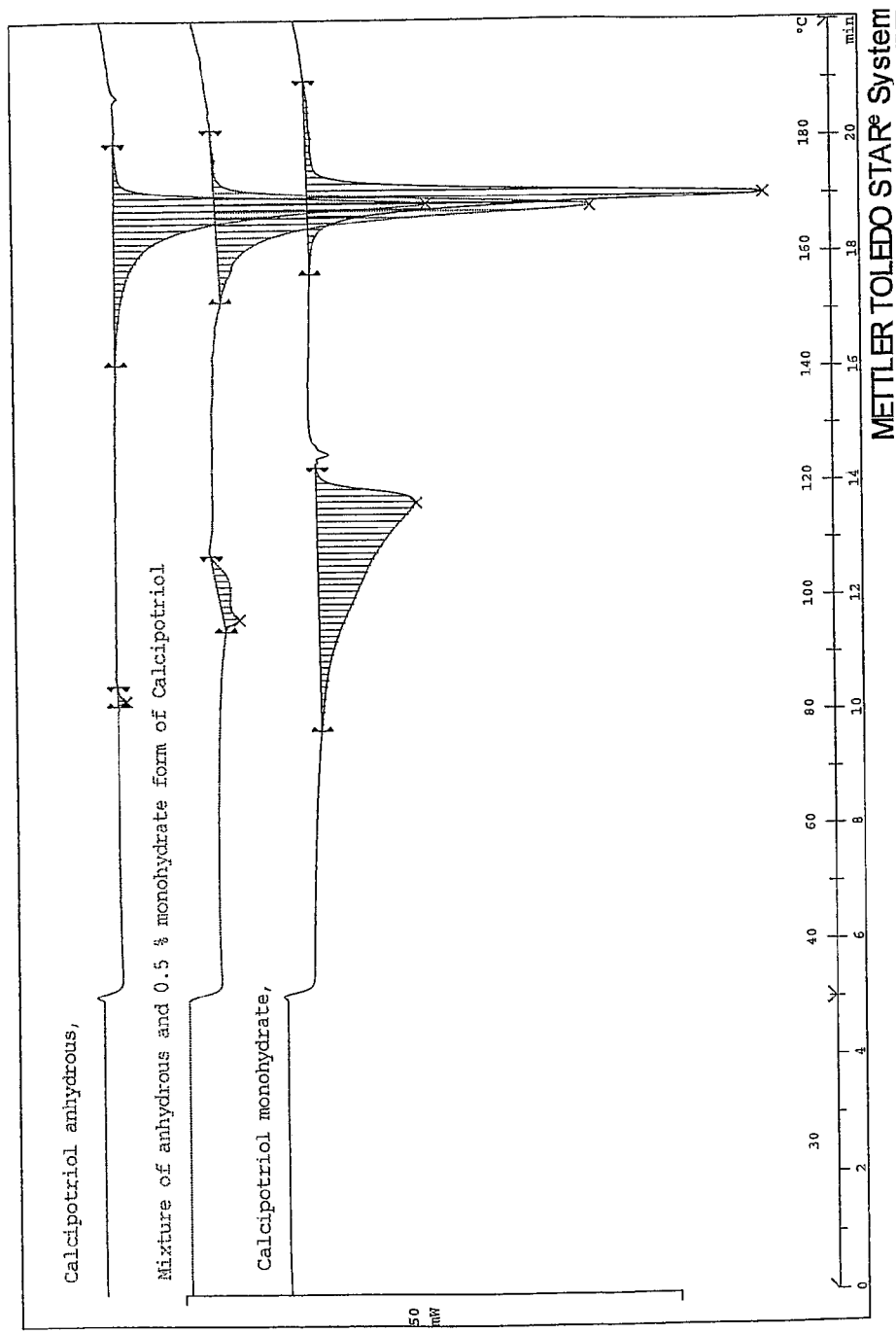
Fig.1. Comparison of DSC curves

PROCESS FOR PREPARATION OF PHARMACEUTICALLY PURE ANHYDROUS CALCIPOTRIOL

CROSS-REFERENCE TO RELATED APPLICATIONS

This is a National Stage Application of International Patent Application No. PCT/PL 2005/000087, with an international filing date of Dec. 29, 2005, which is based on Polish Patent Application Nos. P.372013, filed Dec. 30, 2004.

BACKGROUND OF THE INVENTION

Field of the Invention

The invention relates to the process for preparation of a pharmaceutically pure crystalline form of anhydrous calcipotriol.

Calcipotriol, (1α,3β,5Z,7E,22E,24S)-24-cyclopropyl-9,10-secochola-5,7,10(19),22-tetraene-1,3,24-triol, like other natural vitamin $D_3$ metabolites, such as 1α,24R-dihydroxycholecalciferol (tacalcitol) and 1,25-dihydroxycholecalciferol (calcitriol), shows a strong activity in inhibiting undesirable proliferation of epidermal keratinocytes (F. A. C. M. Castelijns, M. J. Gerritsen, I. M. J. J. van Vlijmen-Willems, P. J. van Erp, P. C. M. van de Kerkhof; *Acta Derm. Venereol.* 79, 111 (1999)). Studies in rats show that calcipotriol has a 100-200 fold weaker effect on calcium metabolism compared to calcitriol (L. Binderup, E. Bramm; *Biochem. Pharmacol.* 37, 889 (1988)), thus clearly limiting the hypercalcemia compared to hypercalcemia observed following the use of calcitriol. The efficacy of calcipotriol in the treatment of psoriasis was shown in a number of clinical trials (US 20010049365 A1, DE 4328217, WO 8700834). The efficacy of calcipotriol in the treatment of acne (EP 1138323 A1), hyperthyroidism (JP 07242550 A2), multiple sclerosis (WO 9528926 A1), tuberculosis (JP 08092098 A2), cancer (WO 9820866 A2, WO 9949870), immune system disorders (U.S. Pat. No. 5,824,313 A), eye diseases (WO 9853806 A1), osteoporosis (WO 9853827 A1, WO 0061123 A2), and in preparations used for the prevention of skin aging (JP 2001288113 A2) has also been shown in clinical trials.

Preparation of calcipotriol was described in an International Patent Application WO 87/00834 (EP 0227826 B1), as well as in M. J. Calverley, *Tetrahedron* 43, 4609 (1987). This method consists of attachment of a C(23)-C(27) side chain to a protected C(22)-aldehyde derivative of (5E)-cholecalciferol in a Wittig type reaction with (cyclopropyl)carbonylmethylene triphenylphosphate. The C(24)-ketone group is then reduced, to give a mixture of C(24)-epimeric alcohols, which are separated by chromatography, giving predominantly the (24R) isomer. The (5E,24S) isomer is then subjected to photoisomerization, to give (5Z,24S) derivative. Deprotection of hydroxyl groups gives calcipotriol.

According to the procedure disclosed in EP 0227826 B1, crude oily calcipotriol is purified by silica gel column chromatography with ethyl acetate as eluent, and then crystallized from methyl formate, to give a crystalline needle structure product with a melting point of 166-168° C.

In practice, the desired isomer of calcipotriol of configuration (5Z,24S), prepared in multi-step synthesis and pre-purified by silica gel chromatography, contains, apart from the product of the reversible isomerisation, i.e., pre-calcipotriol, numerous impurities. The main impurities, being the optical and geometrical isomers of calcipotriol, are, among others: (1α,3β,5Z,7E,22E,24R)-24-cyclopropyl-9,10-secochola-5,7,10(19),22-tetraene-1,3,24-triol {(24R) isomer}, (1α,3β,5Z,7E,22Z,24S)-24-cyclopropyl-9,10-secochola-5,7,10(19),22-tetraene-1,3,24-triol (22,23-cis isomer), and (1α,3β,5E,7E,22E,24S)-24-cyclopropyl-9,10-secochola-5,7,10(19),22-tetraene-1,3,24-triol (5,6-trans isomer).

Product obtained after chromatography, usually in a form of an oil or yellowish solid, is hereinafter referred to as "crude" calcipotriol.

The degree of purity of crude calcipotriol, determined by analytical methods, is often 80% or below.

Pharmaceutically pure calcipotriol, both anhydrous and monohydrate, should meet Pharmacopoeial requirements, set forth in the monograph of the PHARMEUROPA [16(2), April 2004, p. 298 and European Pharmacopoeia 5.3 (2005), p. 3460. The monograph defines the total level of impurities of anhydrous calcipotriol to be maximum 2.0 percent and loss on drying determined by thermogravimetry maximum 1.0 percent.

As a "pharmaceutically pure calcipotriol", throughout the further description, is understood a substance with water content not more than 1.0%, preferably not more than 0.5%, and the level of impurities not more than 2.0%, preferably not more than 1.0%.

A common practice for reducing the level of impurities of the crude substances is multiple crystallization from a defined solvent or a mixture of solvents.

This procedure, although guaranteeing obtaining calcipotriol characterized by low content of impurities (see: a comparative Example 1 of the experimental part), is a laborious and time-consuming one. Moreover, it results in high loss of substance at the consecutive crystallization steps and low yield of the valuable final product. Crystallization, even multiple, does not always guarantee obtaining a moisture-free product. Meanwhile, experimental studies show that calcipotriol obtained after silica gel column chromatography usually contains, apart from the impurities, significant amount of water (usually clearly over 1%), which results from its presence in various solvents and reagents used in the consecutive synthesis steps.

Literature review shows that the crystalline form of calcipotriol clearly affects the stability of the pharmaceutical formulations for topical administration, such as ointments, creams, gels or liquids. Due to its poor stability in some solutions, in pharmaceutical formulations, particularly in creams and gels, using of calcipotriol as suspension of crystals is preferred. For improved control of crystal size, which is a key parameter of calcipotriol release profile reproducibility, the crystalline substance is usually micronized or wet grinded. This process fails in case of crystalline anhydrous calcipotriol prepared by the methods known from the art, due to poor wettability of crystals. Moreover, thus obtained crystals are not fine enough and are characterized by size heterogeneity (see: EP 0679154 B1).

BRIEF SUMMARY OF THE INVENTION

The invention provides a process for the preparation of a pharmaceutical-grade anhydrous calcipotriol comprising: (a) dissolving crude calcipotriol having a water content of X% by weight in a first solvent or in a mixture of two or more first solvents, the first solvent or the mixture of two or more first solvents forming an azeotropic system with water, to obtain a solution of crude calcipotriol; (b) obtaining an intermediate calcipotriol by (i) placing the solution of crude calcipotriol under a reduced pressure and evaporating, if X is greater than or equal to 1, or (ii) crystallizing, if X is lower than 1; and (c) re-dissolving the intermediate calcipotriol in a second solvent or a mixture of two or more second solvents, the second solvent being anhydrous, and crystallizing at least once to obtain pharmaceutical-grade anhydrous calcipotriol.

In certain embodiments of the invention, the first solvent is selected from the group of an aromatic hydrocarbon, an aliphatic hydrocarbon, or an alicyclic hydrocarbon.

In certain embodiments of the invention, the first solvent is selected from the group of toluene, hexane, cyclohexane and methylcyclohexane.

In certain embodiments of the invention, the first solvent is the same as the second solvent; or the mixture of two or more first solvents is the same as the mixture of the second solvents.

In certain embodiments of the invention, the process for the preparation of a pharmaceutical-grade anhydrous calcipotriol comprises re-dissolving the intermediate calcipotriol in a second solvent or a mixture of two or more second solvents, the second solvent being anhydrous, and crystallizing exactly once to obtain pharmaceutical-grade anhydrous calcipotriol.

In certain embodiments of the invention, the second solvent is acetone.

In certain embodiments of the invention, the mixture of the second solvents is a mixture of acetone and hexane.

In certain embodiments of the invention, the mixture of two or more first solvents comprises a solubilizing agent and a first solvent forming an azeotropic system with water.

In certain embodiments of the invention, the solubilizing agent is selected from a group of an aliphatic alcohol, a ketone, an ether, and an ester.

In certain embodiments of the invention, the first solvent forming an azeotropic system with water is toluene.

In certain embodiments of the invention, the first solvent simultaneously forms an azeotropic system with water and solubilizes crude calcipotriol.

In certain embodiments of the invention, the first solvent tetrahydrofuran.

In certain embodiments of the invention, the mixture of two or more first solvents is a mixture of acetone and hexane, a mixture of toluene and ethanol, a mixture of toluene and ethyl acetate, a mixture of methyl isobutyl ketone and toluene, a mixture of t-butyl methyl ether and toluene, a mixture of n-propyl methyl ketone and toluene, or a mixture of n-butyl acetate and toluene.

In certain embodiments of the invention, the mixture of two or more second solvents is a mixture of ethyl acetate and toluene, or a mixture of acetone and hexane.

In certain embodiments of the invention, the second solvent is acetone, 1-chlorobutane, methyl isobutyl ketone, t-butyl methyl ether, n-propyl methyl ketone, or n-butyl acetate.

In certain embodiments of the invention, the water content is determined by HPLC.

In other aspects, the invention provides a pharmaceutical-grade anhydrous calcipotriol obtained by the processes described herein.

In certain embodiments of the invention, the pharmaceutical-grade anhydrous calcipotriol has a water content of less than 1% by weight, or of less than 0.5% by weight.

BRIEF DESCRIPTION OF THE DRAWINGS

The objects and advantages of the present invention will become more readily apparent after reading the ensuing description of the non-limiting illustrative embodiment and viewing the accompanying drawings, in which FIG. 1 shows a comparison of DSC curves of anhydrous calcipotriol and calcipotriol monohydrate.

DETAILED DESCRIPTION OF THE INVENTION

The process according to the present invention, due to a special purification method and the suitably selected solvents used in it, solves the problem of insufficient homogeneity of anhydrous calcipotriol crystals as well as its chemical purity. We have unexpectedly found that processing according to a present invention not only enables to obtain crystalline calcipotriol of pharmaceutical grade and low moisture content, but also solves the problem of heterogeneity of crystals in anhydrous calcipotriol known from the art.

A process for the preparation of a pharmaceutical-grade anhydrous calcipotriol according to the invention comprises: (a) dissolving crude calcipotriol having a water content of X% by weight in a first solvent or in a mixture of two or more first solvents, said first solvent or said mixture of two or more first solvents forming an azeotropic system with water, to obtain a solution of crude calcipotriol; (b) obtaining an intermediate calcipotriol by (i) placing said solution of crude calcipotriol under a reduced pressure and evaporating, if X is greater than or equal to 1, or (ii) crystallizing, if X is lower than 1; and (c) re-dissolving said intermediate calcipotriol in a second solvent or a mixture of two or more second solvents, said second solvent being anhydrous, and crystallizing at least once to obtain pharmaceutical-grade anhydrous calcipotriol.

Suitable solvents to be used for calcipotriol purification and dehydration are selected by the person skilled in the art on the basis of the degree of the product's purity, which purity affects its physical form and capacity to dissolve. Depending on circumstances, the use of a single solvent might be sufficient, or the use of two solvents, of which one is used as a solubilizing agent, may be needed. Calcipotriol prepared by a synthetic method and silica gel chromatography, containing numerous by-products, incompletely removed eluent, etc., may require the use of a mixture of solvents for purification. In the case calcipotriol is in a solid form and requires only final purification prior to use for preparation of pharmaceutical formulations, a single solvent is sufficient.

Generally, the types and proportions of solvents used may be selected by the person skilled in the art with respect to the solubility of crude calcipotriol and the ability of the solvents to form azeotropic systems. Preferred solvent mixture should have a composition ensuring removal of all moisture and a low boiling point of the azeotropic system.

In one embodiment of the invention, a two-component mixture of solvents is used, of which one is a solubilizing agent, and the other forms an azeotropic system with water.

Examples of preferred solubilizing solvents are aliphatic alcohols, such as methanol and ethanol; ketones, such as methyl isobutyl ketone, n-propyl methyl ketone; esters, such as ethyl acetate, n-butyl acetate; and aliphatic and cyclic ethers, such as tert-butyl methyl ether or tetrahydrofuran. The role of a solubilizing solvent may also play the eluent, present in the crude product obtained after chromatography, such as ethyl acetate, which is not evaporated to dryness in the process of concentration of the eluate.

The other component of a solvent mixture is any solvent which forms an azeotropic system with water, provided it is pharmaceutically acceptable.

Pharmaceutically acceptable solvents which form azeotropic systems with water, are, without limitation, acetonitrile, methylene chloride, cyclohexane, dioxane, ethanol, diethyl ether, isopropanol, hexane, methylcyclohexane, ethyl acetate, tetrahydrofuran and toluene.

Preferred solvents forming azeotropic systems with water, useful in the process according to the invention, are toluene, methylcyclohexane, cyclohexane, hexane and tetrahydrofuran.

Generally, the choice of a solvent or mixture of solvents resides in the experience of the person skilled in the art, and is based on available literature data.

The preferred solvent mixtures in the process according to the present invention are, without limitation, ethyl acetate-toluene, ethanol-toluene, or acetone-hexane.

In another embodiment of the process according to the invention, crude calcipotriol is dissolved in a single solvent, being an efficient solubilizer for the product and forming an azeotropic system with water at the same time. Preferred solvent in this embodiment of the invention is tetrahydrofuran.

The choice of a procedure according to variant (i) or (ii) of the invention is based on the preliminary evaluation of the level of impurities in the crude calcipotriol to be purified, as determined by an analytical method, e.g. thin-layer chromatography (TLC) and/or high pressure liquid chromatography (HPLC) and a visual evaluation of the sample.

In the case of purification of calcipotriol of high water content, solvents are removed azeotropically from the solution containing calcipotriol, to give calcipotriol as clear oil. In the case of lower water content, the solution is allowed to crystallize to a crystalline product, at low temperature.

The product obtained in i) or ii), as clear oil or in a solid form, is then crystallized from an anhydrous solvent or a mixture of anhydrous solvents. Crystallization solvents may be the same or different solvents or their mixtures as those used in the water-removal step.

Preferred crystallization solvents are aliphatic ketones, such as acetone; or esters, such as ethyl acetate, alternatively in a mixture with aliphatic saturated hydrocarbons, such as hexane; alicyclic hydrocarbons, such as cyclohexane; or aromatic hydrocarbons, such as toluene.

Preferably, the crystallization solvent is acetone, or a mixture of acetone and hexane.

In the case of procedure according to variant b), single crystallization of calcipotriol from an anhydrous solvent or mixture of anhydrous solvents is sufficient for obtaining a product of water content (determined by coulometry) below 1.0% and the level of impurities complying with pharmacopoeial monograph. In the case of procedure according to variant a), one or more than one crystallization may be required to achieve a similar beneficial effect.

Anhydrous calcipotriol obtained by the process according to the invention is characterized by a unique crystalline structure differentiating it from the other vitamin D analogs.

Crystal structure of anhydrous calcipotriol, registered at Cambridge Crystallographic Data Centre under deposit number CCDC 240113, is fundamentally different than the structure of calcipotriol monohydrate described in EP 0679154 B1. In the crystal structure of anhydrous calcipotriol no position is occupied by water molecules or solvents used for crystallization. Several hydrogen bonding are present involving all three hydroxyl groups of calcipotriol. The observed lengths of hydrogen bonds indicate that anhydrous calcipotriol might be expected in a crystalline state as a fairly stable substance.

The thermogravimetric behavior of anhydrous calcipotriol and calcipotriol monohydrate are recorded by differential scanning calorimetry (DSC). The comparison of DSC curves, presented in FIG. 1, shows a very distinct difference between anhydrous calcipotriol and calcipotriol monohydrate. The DSC curve obtained for anhydrous sample shows small endothermic signal related to the melting of substance at ~165° C. The melting point is taken to be the start as onset of the melting process which is defined as the temperature given by the intercept of the extrapolated slope of the melting curve and continuation of the base line. For monohydrate sample two endothermic signals, first related to water content (~98° C.) and second related to melting of the substance are observed. For a comparison, the DSC curve obtained of a mixture of anhydrous form with the addition of 0.5% calcipotriol monohydrate presents, similarly to the monohydrate sample, two signals: a first one related to monohydrate content together with acetone peak shifted in high temperature direction, and a second one related to the melting of the substance.

The process according to the invention yields calcipotriol of water content below 1.0%, preferably below 0.5% and impurities content below 2.0%, preferably below 1.0%.

The process according to the invention allows for the preparation of anhydrous calcipotriol in a suitable fine crystalline form, which facilitates the removal of solvents residue below the level admissible for a pharmaceutically pure substance. Due to a combination of its hydrophobic and lipophilic properties, anhydrous calcipotriol prepared in the process according to the invention may be used for the preparation of pharmaceutical formulations, especially topical formulations, without any additional processes, such as micronization.

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

The following examples are provided to illustrate the invention. The examples are not meant to limit the scope of the invention as defined in the claims.

EXAMPLES

Example 1

Prior Art

Crude calcipotriol (3.1 g), obtained after column chromatography (silica gel, ethyl acetate as eluent) in the form of a foamy oil (HPLC purity ca. 80%), was dissolved in 25 mL of boiling ethyl acetate under argon and a solution was allowed to crystallize (1 h at room temperature and 24 h at −30° C.). The solution was decanted, and the crystals were washed with 1 portion of cold ethyl acetate (5 mL). The residue was dried to a solid mass on a vacuum oil pump. Obtained was 1.8 g of crystalline product. This product was dissolved in 20 mL of boiling ethyl acetate under argon and left to crystallize (1 h at room temperature and 24 h at −30° C.). The solution was decanted and crystals were washed with 1 portion of cold ethyl acetate (5 mL), dried to a solid mass on vacuum oil pump to give 1.17 g of crystalline product. The product was again dissolved in 18 mL of boiling ethyl acetate, quickly filtered through a Schott funnel, and the funnel was washed with 1 mL of warm ethyl acetate. The flask was left for crystallization under argon (1 hour at room temperature and 24 hours at −30° C.). The solution was decanted, and crystals washed with 1 portion of cold ethyl acetate (4 mL) and dried to a solid mass on a vacuum oil pump. Obtained was 0.96 g of a crystalline product. The product was again dissolved in 18 ml, of boiling ethyl acetate and left to crystallize under argon (1 h at room temperature and 24 h at −30° C.). The solution was decanted and crystals washed with 1 portion of cold ethyl acetate (4 mL) and dried to a solid mass on a vacuum oil pump. Obtained was 0.89 g crystalline anhydrous calcipotriol (water content by coulometry 0.26%).

Example 2

Calcipotriol (200 mg) after purification by silica gel column chromatography (HPLC purity ca. 95%, water content over 1%), was dissolved in a hot mixture of anhydrous acetone (2.5 mL) and anhydrous hexane (1.5 mL) under argon. The solution was cooled at room temperature under argon and the solution was allowed to crystallize at 0° C. for ca. 16 h. Calcipotriol crystals were filtered under reduced pressure and dried under vacuum at room temperature to a solid mass. Obtained was 180 mg of crystalline anhydrous calcipotriol (water content by coulometry 0.79%).

Example 3

Calcipotriol (5 g), obtained by removing eluent of a flash chromatography, as yellowish solid (HPLC purity ca. 80%), was dissolved in 300 mL of toluene:anhydrous ethanol mixture (5:1 v/v). The solution was filtered to remove mechanical impurities, and solvents were azeotropically removed under reduced pressure at room temperature. The resulting foamy oil was dried for 30 minutes on oil pump, and dissolved in 80 mL of degassed and saturated with argon acetone, heated to 40° C. The solution was then concentrated in an inert gas atmosphere to get first crystals. The solution was allowed to crystallize under dark conditions and argon atmosphere for 2 hours, and then for 18 h at 5° C. The obtained crystalline solid was filtered off and dried under reduced pressure for ca. 7-8 h. Obtained was 3.7 g of calcipotriol as white crystalline powder of HPLC purity 98-99.5%, demonstrating a DSC single endothermic peak at 165° C. and water content by coulometry 0.28%.

Example 4

Crude oily calcipotriol (5.3 g) was diluted with 6 mL of ethyl acetate and 3 mL of anhydrous toluene was added. Solvents were evaporated azeotropically under reduced pressure. The oily residue was dissolved in 5 mL of ethyl acetate and 4 mL of anhydrous toluene was added. The solution was allowed to crystallize under argon at room temperature for 2 hours and for 1 hour at −20° C. The resulting crystalline solid was filtered off under reduced pressure and washed on the funnel with 5 mL of cold ethyl acetate. Solvent residue was removed under vacuum. Obtained was 1.77 g (67%) of fine crystalline white anhydrous calcipotriol (water content by coulometry 0.21%).

Example 5

Crude oily calcipotriol after column chromatography (236 mg, HPLC purity 96%) was dissolved in 7 mL of anhydrous ethanol and 2.5 mL of anhydrous toluene was added. The solvents were azeotropically removed under reduced pressure and 12 mL of 1-chlorobutane was added to the resulting solution until cloudiness was observed. The solution was heated and, when clear, left to crystallize under an argon atmosphere for 1 hour at room temperature and then for 1 hour at 0° C. The resulting crystalline solid was filtered off under reduced pressure and dried under reduced pressure. Obtained was 190 mg (80% yield) of fine crystalline white anhydrous calcipotriol of purity complying with pharmacopoeial monograph (substance content 98.33%; water content by coulometry 0.30%).

Example 6

Crude calcipotriol obtained after column chromatography (200 mg, from mother liquors, HPLC purity ca. 70%), was dissolved in 16 mL of anhydrous ethanol and 3 mL of anhydrous toluene was added. The solution was azeotropically concentrated under reduced pressure to half volume and 15 mL of 1-chlorobutane was added. The resulting solution was concentrated under reduced pressure until cloudiness was observed. The solution was allowed to crystallize under argon at room temperature for 1 hour and at 0° C. for 1 hour. The product was then filtered off and dried under reduced pressure. Obtained was 135 mg of fine, white calcipotriol solid of water content determined by coulometry 0.18%. The filtrate was concentrated at room temperature by removing solvents in a stream of argon; and the concentrate was left to crystallize for 1 hour at 0° C. II crop of calcipotriol crystals was filtered off and dried under reduced pressure. Obtained was 20 mg of fine crystalline white anhydrous calcipotriol (water content by coulometry 1%). Total yield of crystallization 77%, HPLC purity>95%.

Example 7

Crude calcipotriol (228 mg, HPLC purity ca. 70%), was dissolved in 10 mL of hot methyl isobutyl ketone and 12 mL of anhydrous toluene was added. Solvents were removed azeotropically under reduced pressure and 5 mL of methyl isobutyl ketone was added to the oily residue. The solution was allowed to crystallize under argon for 1 hour at room temperature and for 24 hours at −20° C. The resulting crystalline solid was filtered off and dried under reduced pressure. Obtained was 194 mg (85%) of fine crystalline white anhydrous calcipotriol of HPLC purity 97-98%.

Example 8

Calcipotriol (220 mg, HPLC purity ca. 70%), was dissolved in 15 mL of hot t-butyl methyl ether and 10 mL of anhydrous toluene was added. Solvents were removed azeotropically under reduced pressure and 5 mL of t-butyl methyl ether was added to the oily residue. The solution was allowed to crystallize under argon for 1 hour at room temperature and for 24 hours at −20° C. The resulting crystalline solid was filtered off and dried under reduced pressure. Obtained was 180 mg (82%) of fine crystalline white anhydrous calcipotriol of purity complying with pharmacopoeial monograph.

Example 9

Calcipotriol (118 mg) was dissolved in 7 mL of hot n-propyl methyl ketone and 3 mL of anhydrous toluene was added. Solvents were removed azeotropically under reduced pressure and 3 mL of n-propyl methyl ketone was added to the oily residue. The solution was allowed to crystallize under argon for 2 hours at room temperature and for 24 hours at 0° C. The resulting crystalline solid was filtered off and dried under reduced pressure. Obtained was 100 mg (85%) of fine crystalline white anhydrous calcipotriol of purity complying with pharmacopoeial monograph.

Example 10

Calcipotriol (120 mg) was dissolved in 6 mL of n-butyl acetate and 3 mL of anhydrous toluene was added. The solvents were removed azeotropically under reduced pressure and 3 mL of n-butyl acetate was added to the oily residue. The solution was allowed to crystallize under argon for 2 hours at room temperature and for 24 hours at 0° C. The resulting crystalline solid was filtered off and dried under reduced pressure. Obtained was 80 mg (67%) of fine crystalline white anhydrous calcipotriol of purity complying with pharmacopoeial monograph.

Example 11

To 160 mg of crude calcipotriol, obtained after concentration of eluates from column chromatography, 5 mL of cyclohexane was added and the solution was dried by azeotropic distillation under reduced pressure at 45° C. The product was dissolved under argon in a hot mixture of 2.5 mL of anhydrous acetone and 1.5 mL of anhydrous hexane. The solution was cooled at room temperature under argon and left to crystallize for ca. 16 hours at 0° C. The obtained crystals were filtered under reduced pressure and dried under vacuum at room temperature to a solid mass. The water content in the obtained product determined by coulometry was 0.91%.

Example 12

To 150 mg of crude calcipotriol, obtained after concentration of eluates from column chromatography, 5 mL of methylcyclohexane was added and dried by azeotropic distillation under reduced pressure at 45° C. The resulting product was then recrystallized under argon from the mixture of acetone-hexane (2:1 v/v) at 0° C. for 24 hours. The resulting solid was dried under reduced pressure at room temperature to a solid mass. The water content in the obtained product determined by coulometry was 0.90%.

Example 13

To 180 mg of crude calcipotriol 5 mL of anhydrous tetrahydrofuran was added and the solution was dried by azeotropic distillation under reduced pressure, at 45° C. The resulting product was then crystallized under argon from acetone-hexane mixture (2:1 v/v) at 0° C. for 24 hours. The resulting solid was dried under reduced pressure at room temperature to a solid mass. The water content in the obtained product determined by coulometry was 0.97%.

The invention claimed is:

1. A process for the preparation of a pharmaceutical-grade anhydrous calcipotriol comprising:
   (a) dissolving crude calcipotriol having a water content of X% by weight in a first solvent or in a mixture of two or more first solvents, said first solvent or said mixture of two or more first solvents forming an azeotropic system with water, to obtain a solution of crude calcipotriol;
   (b) obtaining an intermediate calcipotriol by (i) placing said solution of crude calcipotriol under a reduced pressure and evaporating, if X is greater than or equal to 1, or (ii) crystallizing, if X is lower than 1; and
   (c) re-dissolving said intermediate calcipotriol in a second solvent or a mixture of two or more second solvents, said second solvent being anhydrous, and crystallizing at least once to obtain pharmaceutical-grade anhydrous calcipotriol.

2. The process of claim 1, wherein said first solvent is selected from the group of an aromatic hydrocarbon, an aliphatic hydrocarbon, or an alicyclic hydrocarbon.

3. The process of claim 2, wherein said first solvent is selected from the group of toluene, hexane, cyclohexane and methylcyclohexane.

4. The process of claim 1, wherein said first solvent is the same as said second solvent; or said mixture of two or more first solvents is the same as said mixture of said second solvents.

5. The process of claim 1, wherein in (c) crystallizing exactly once.

6. The process of claim 1, wherein said second solvent is acetone; or said mixture of said second solvents is a mixture of acetone and hexane.

7. The process of claim 1, wherein said mixture of two or more first solvents comprises a solubilizing agent and a first solvent forming an azeotropic system with water.

8. The process of claim 7, wherein said solubilizing agent is selected from a group of an aliphatic alcohol, a ketone, an ether, and an ester.

9. The process of claim 7, wherein said first solvent forming an azeotropic system with water is toluene.

10. The process of claim 8, wherein said first solvent forming an azeotropic system with water is toluene.

11. The process of claim 1, wherein said first solvent simultaneously forms an azeotropic system with water and solubilizes crude calcipotriol.

12. The process of claim 1, wherein said first solvent is tetrahydrofuran.

13. The process of claim 1, wherein said mixture of two or more first solvents is a mixture of acetone and hexane, a mixture of toluene and ethanol, a mixture of toluene and ethyl acetate, a mixture of methyl isobutyl ketone and toluene, a mixture of t-butyl methyl ether and toluene, a mixture of n-propyl methyl ketone and toluene, or a mixture of n-butyl acetate and toluene.

14. The process of claim 1, wherein said mixture of two or more second solvents is a mixture of ethyl acetate and toluene, or a mixture of acetone and hexane.

15. The process of claim 1, wherein said second solvent is acetone, 1-chlorobutane, methyl isobutyl ketone, t-butyl methyl ether, n-propyl methyl ketone, or n-butyl acetate.

16. The process of claim 1, wherein said water content is determined by HPLC.

17. The process of claim 1, wherein said calcipotriol obtained in (c) has a water content of less than 1% by weight.

18. The process of claim 17, wherein said calcipotriol obtained in (c) has a water content of less than 0.5% by weight.

19. A process for the preparation of a pharmaceutical-grade anhydrous calcipotriol comprising:
   (a) dissolving crude calcipotriol having a water content of X% by weight in a first solvent or in a mixture of two or more first solvents, said first solvent or said mixture of two or more first solvents forming an azeotropic system with water, to obtain a solution of crude calcipotriol;
   followed by (b) obtaining an intermediate calcipotriol by (i) placing said solution of crude calcipotriol under a reduced pressure and evaporating, if X is greater than or equal to 1, or (ii) crystallizing, if X is lower than 1; and followed by (c) re-dissolving said intermediate calcipotriol in a second solvent or a mixture of two or more second solvents, said second solvent being anhydrous, and crystallizing at least once to obtain pharmaceutical-grade anhydrous calcipotriol.

20. The process of claim 19, wherein said first solvent is selected from the group of an aromatic hydrocarbon, an aliphatic hydrocarbon, or an alicyclic hydrocarbon.

21. The process of claim 20, wherein said first solvent is selected from the group of toluene, hexane, cyclohexane and methylcyclohexane.

22. The process of claim 19, wherein said first solvent is the same as said second solvent; or said mixture of two or more first solvents is the same as said mixture of said second solvents.

23. The process of claim 19, wherein in (c) crystallizing exactly once.

24. The process of claim 19, wherein said second solvent is acetone; or said mixture of said second solvents is a mixture of acetone and hexane.

25. The process of claim 19, wherein said mixture of two or more first solvents comprises a solubilizing agent and a first solvent forming an azeotropic system with water.

26. The process of claim 25, wherein said solubilizing agent is selected from a group of an aliphatic alcohol, a ketone, an ether, and an ester.

27. The process of claim 25, wherein said first solvent forming an azeotropic system with water is toluene.

28. The process of claim 26, wherein said first solvent forming an azeotropic system with water is toluene.

29. The process of claim 19, wherein said first solvent simultaneously forms an azeotropic system with water and solubilizes crude calcipotriol.

30. The process of claim 19, wherein said first solvent is tetrahydrofuran.

31. The process of claim 19, wherein said mixture of two or more first solvents is a mixture of acetone and hexane, a mixture of toluene and ethanol, a mixture of toluene and ethyl acetate, a mixture of methyl isobutyl ketone and toluene, a mixture of t-butyl methyl ether and toluene, a mixture of n-propyl methyl ketone and toluene, or a mixture of n-butyl acetate and toluene.

32. The process of claim 19, wherein said mixture of two or more second solvents is a mixture of ethyl acetate and toluene, or a mixture of acetone and hexane.

33. The process of claim 19, wherein said second solvent is acetone, 1-chlorobutane, methyl isobutyl ketone, t-butyl methyl ether, n-propyl methyl ketone, or n-butyl acetate.

34. A process for the preparation of a pharmaceutical-grade anhydrous calcipotriol comprising:
 (a) dissolving crude calcipotriol having a water content of greater than 1% by weight in a first solvent or in a mixture of two or more first solvents, said first solvent or said mixture of two or more first solvents forming an azeotropic system with water, to obtain a solution of crude calcipotriol;
 (b) obtaining an intermediate calcipotriol by placing said solution of crude calcipotriol under a reduced pressure and evaporating; and
 (c) re-dissolving said intermediate calcipotriol in a second solvent or a mixture of two or more second solvents, said second solvent being anhydrous, and crystallizing at least once to obtain pharmaceutical-grade anhydrous calcipotriol.

* * * * *